US007348341B2

(12) United States Patent
Sanganee et al.

(10) Patent No.: US 7,348,341 B2
(45) Date of Patent: *Mar. 25, 2008

(54) CHEMICAL COMPOUNDS

(75) Inventors: Hitesh Sanganee, Loughborough (GB); Brian Springthorpe, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 142 days.

This patent is subject to a terminal disclaimer.

(21) Appl. No.: 10/296,034

(22) PCT Filed: May 30, 2001

(86) PCT No.: PCT/SE01/01298

§ 371 (c)(1),
(2), (4) Date: Nov. 20, 2002

(87) PCT Pub. No.: WO01/92227

PCT Pub. Date: Dec. 6, 2001

(65) Prior Publication Data

US 2003/0166652 A1 Sep. 4, 2003

(30) Foreign Application Priority Data

May 31, 2000 (GB) ................... 0013060.9

(51) Int. Cl.
A61K 31/445 (2006.01)
C07D 401/12 (2006.01)
(52) U.S. Cl. ............... 514/318; 514/326; 514/331; 546/193; 546/212; 546/229
(58) Field of Classification Search ......... 514/318, 514/326, 331; 546/193, 212, 229
See application file for complete search history.

(56) References Cited

U.S. PATENT DOCUMENTS

| 4,335,127 | A | 6/1982 | Vandenberk et al. ... 514/266.22 |
| 4,853,393 | A | 8/1989 | Zimmermann ............. 514/318 |
| 5,143,923 | A | 9/1992 | Hrib et al. ................ 514/321 |
| 5,210,086 | A | 5/1993 | George et al. ............. 514/275 |
| 6,140,344 | A | 10/2000 | Gong et al. ............... 514/317 |
| 6,518,286 | B1 | 2/2003 | Baxter et al. .............. 514/327 |
| 6,946,478 | B2 | 9/2005 | Baxter et al. .............. 514/327 |
| 2003/0050309 | A1 | 3/2003 | Aquila et al. ............. 514/227.5 |

FOREIGN PATENT DOCUMENTS

| EP | 0124476 A1 | 11/1984 |
| EP | 0184258 A2 | 6/1986 |
| EP | 0288563 A1 | 11/1988 |
| EP | 0 429 341 A2 | 5/1991 |
| EP | 0 429 341 A3 | 5/1991 |
| EP | 0515240 | 11/1992 |
| EP | 0661266 | 7/1995 |
| EP | 0903349 | 3/1999 |
| FR | 2 675 801 A1 | 10/1992 |
| FR | 2724382 A1 | 3/1996 |
| GB | 1243991 | 8/1971 |
| JP | 09040646 | 2/1997 |
| JP | 09077742 | 3/1997 |
| JP | 03264579 | 11/1999 |
| WO | WO96/14317 | 5/1996 |
| WO | WO 96/29330 | 9/1996 |
| WO | WO 97/10207 | 3/1997 |
| WO | WO 97/42956 | 11/1997 |
| WO | WO 97/49680 | 12/1997 |
| WO | WO99/04794 | 2/1999 |
| WO | WO 99/37617 | 7/1999 |
| WO | WO 99/37619 | 7/1999 |
| WO | WO 99/38514 | 8/1999 |
| WO | WO 00/29377 | 5/2000 |
| WO | WO 00/35877 | 6/2000 |
| WO | WO 00/58305 | 10/2000 |
| WO | WO 01/14333 | 3/2001 |
| WO | WO02/20484 | * 3/2002 |
| WO | WO 02/30899 | 4/2002 |
| WO | WO 03/018556 | * 3/2003 |
| WO | WO03/18556 | * 3/2003 |
| WO | WO 03/18566 | 3/2003 |

OTHER PUBLICATIONS

Bundgaard "Design of prodrugs" p. 1 (1986).*
Cohen et al. "Cytokine function . . . " CA 125:3527 (1996).*
King "Medicinal chemistry: principle and practice" p. 206-209 (1994).*
Rubini et al. "Synthesis of isosteric methylen-oxy . . . " Tetrahedron v. 42, p. 6039-45 (1986).*
Ian T. Forbes et al., "(R)-3, N-Dimethyl-N-[1-methyl-3-(4-methylpiperidin-1-yl)propyl]benzenesulfonamide: The First Selective 5-HT$_7$ Receptor Antagonist" 41 Journal of Medicinal Chemistry 5, 655-657 (1998).
Jean-Luc Malleron et al., "New Indole Derivatives as Potent and Selective Serotonin Uptake Inhibitors" 36 J. Med. Chem. 1194-1202 (1993).
Maria López-Rodriguez et al., "First Pharmacophoric Hypothesis for 5-HT Antagonism" 10 Bioorganic & Medicinal Chemistry Letters 1097-1100 (2000).
Acs et al., "Preparation of N-(4-piperidinylbutyl)carboxamides as D3 receptor agonists for treatmant of CNS and ophthalmic disorders", CAPLUS, Accession No. 2003:282395; Document No. 138:287532, 2003, 2 pages.
Baxter, "Preparation of piperidinyl compounds as modulators of chemokine receptor activity", CAPLUS, Accession No. 2000:707161; Document No. 133:266738, 2000, 7 pages.
CAS printout for Kikuchi et al., Chem. Abs. 128:22926 (JP 09291090).

(Continued)

Primary Examiner—Celia Chang
(74) Attorney, Agent, or Firm—Fish & Richardson P.C.

(57) ABSTRACT

The invention concerns compounds of formula (I), and their use in therapy, particularly in the modulation of CCR3 activity.

16 Claims, No Drawings

OTHER PUBLICATIONS

CAS printout for Takahashi et al., *Chem Abs.* 128:294706 (JP 10077271).

CAS printout for Vandenberk et al., *Chem Abs.* 97:856 (1982).

Emonds-Alt et al., "Preparation of N-(aminoalkyl)piperidines, their enantiomers, and pharmaceutical compositions as neurokinin receptor antagonists", CAPLUS Accession No. 1993:408684; Document No. 119:8684.

Herndon et al., "Ketanserin Analogues: Structure-Affinity Relationships for 5-HT$_2$ and 5-HT$_{IC}$ Serotonin Receptor Binding", *J. Med. Chem.* 35:4903-4910 (1992).

Hrib et al., "Benzisoxazole-and Benzisothiazole-3-carboxamides as Potential Atypical Antipsychotic Agents", *J. Med. Chem.* 37:2308-2314 (1994).

Jansson et al., "Synthesis of $^3$H and $^{14}$C Ketanserin", *Journal of labelled Components and Radiopharmaceuticals* XXV(7):783-792 (1988).

Nakazato et al., *Chem. Abs.* 126:8111 (WO 9629330).

STN International, File CAPLUS, accession No. 1996:113480, Document No. 124:220549, Kharkovskij Farmatsevticheskij Institut: "Piperdylamide of 3,5-dibromo-4-aminobenzene-sulfonylaminosuccinic acid which produces neuroptic and diuretic effects", & SU, A1, 1824396, Jun. 30, 1993, 2 pages.

CAS ONLINE on STN, Chem. Abstr., Accession No. 1980:586265, Carissimi et al. Farmaco, edizon Scientifica (1980), 35(6), 504-26, abstract only.

* cited by examiner

CHEMICAL COMPOUNDS

CROSS REFERENCE TO RELATED APPLICATIONS

The present application is a national phase application under 35 U.S.C. Section 371 filed from International Patent Application PCT/SE01/01298, filed 30 May 2001, which claims priority to United Kingdom patent application Serial. No. 0013060.9, filed 31 May 2000. The contents of these applications are incorporated herein by reference in their entirety.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/29377.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The present invention provides a compound of formula (I):

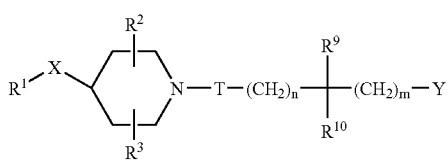

wherein:

m and n are, independently, 0, 1, 2, 3 or 4;
X is $CH_2$, CO, O, S, S(O), $S(O)_2$ or $NR^6$;
Y is $NR^4S(O)_2R^5$ or $S(O)_2NR^4R^5$;
T is C=O or $CR^7R^8$;
$R^1$ is hydrogen, $C_{1-6}$ alkyl, aryl or heterocyclyl;
$R^2$ and $R^3$ are, independently, hydrogen or $C_{1-6}$ alkyl;
$R^4$ and $R^6$ are, independently, hydrogen or $C_{1-6}$ alkyl (optionally substituted with aryl);
$R^5$ is $C_{1-6}$ alkyl {optionally substituted by halogen, $CO_2R^{11}$, aryl or heterocyclyl}, $C_{3-10}$ cycloalkyl {optionally substituted by $C_{1-4}$ alkyl or oxo}, $C_{3-7}$ cycloalkenyl (optionally substituted by $C_{1-6}$ alkyl or aryl), aryl or heterocyclyl; or, when Y is $S(O)_2NR^4R^5$, $R^5$ may also be hydrogen;
$R^7$, $R^8$, $R^9$ and $R^{10}$ are, independently, hydrogen or $C_{1-6}$ alkyl (optionally substituted with aryl);
wherein the foregoing aryl and heterocyclyl moieties are, independently, optionally substituted by one or more of halo, cyano, nitro, hydroxy, $S(O)_qR^{11}$, $OCONR^{12}R^{13}$, $NR^{14}R^{15}$, $NR^{16}COR^{17}$, $NR^{18}CONR^{19}R^{20}$, $SO_2NR^{21}R^{22}$, $NR^{23}SO_2R^{24}$, $CONR^{25}R^{26}$, $COR^{27}$, $CO_2R^{28}$, $OCOR^{29}$, $NR^{30}CO_2R^{31}$, $C_{1-6}$ alkyl (itself optionally substituted with halo, $C_{1-6}$ alkoxy, $C_{3-10}$ cycloalkyl, $CO_2(C_{1-6}$ alkyl), OCO ($C_{1-6}$ alkyl), $SO_2R^{32}$, $CONR^{33}R^{34}$, phenyl, phenoxy, heterocyclyl or heterocyclyloxy), $C_{3-10}$ cycloal, $C_{1-6}$ alkoxy, $C_{1-6}$ haloalkoxy, $C_{2-6}$ alkenyl, $C_{2-6}$ alkynyl, methylenedioxy, phenyl, phenoxy, phenylthio, phenyl($C_{1-4}$)alkoxy, heterocyclyl, heterocyclyloxy or heterocyclyl($C_{1-4}$) alkoxy; wherein any of the immediately foregoing phenyl and heterocyclyl moieties are optionally substituted with halo, hydroxy, nitro, $S(O)_kC_{1-4}$ alkyl, $SO_2NH_2$, cyano, $C_{1-4}$ alkyl, $C_{1-4}$ alkoxy, $CONH_2$, $CONH(C_{1-4}$ alkyl), $CO_2H$, $CO_2(C_{1-4}$ alkyl), $NHCO(C_{1-4}$ alkyl), $NHSO_2(C_{1-4}$ alkyl), $CO(C_{1-4}$ alkyl), $CF_3$ or $OCF_3$;
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{26}$, $R^{27}$, $R^{28}$, $R^{29}$, $R^{30}$, $R^{31}$, $R^{33}$, and $R^{34}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy);
$R^{11}$, $R^{24}$ and $R^{32}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy);
k and q are, independently, 0, 1 or 2;
or a pharmaceutically acceptable salt thereof; or a solvate thereof.

In one particular aspect the present invention provides a compound of formula (I')

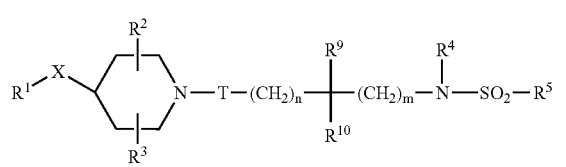

wherein:
m and n are, independently, 0, 1, 2, 3 or 4;
X is $CH_2$, CO, O, S, S(O), $S(O)_2$ or $NR^6$;
T is C=O or $CR^7R^8$;
$R^1$ is hydrogen, $C_{1-6}$ alkyl, aryl or heterocyclyl;
$R^2$ and $R^3$ are, independently, hydrogen or $C_{1-6}$ alkyl;
$R^4$ and $R^6$ are, independently, hydrogen or $C_{1-6}$ alkyl (optionally substituted with aryl);

$R^5$ is $C_{1-6}$ alkyl {optionally substituted by halogen, $CO_2R^{11}$, aryl or heterocyclyl}, $C_{3-10}$ cycloalkyl {optionally substituted by $C_{1-4}$ alkyl or oxo}, $C_{3-7}$ cycloalkenyl {optionally substituted by $C_{1-6}$ alkyl or aryl}, aryl or-heterocyclyl;

$R^7$, $R^8$, $R^9$ and $R^{10}$ are, independently, hydrogen or $C_{1-6}$ alkyl (optionally substituted with aryl);

wherein the foregoing aryl and heterocyclyl moieties are, independently, optionally substituted by one or more of halo, cyano, nitro, hydroxy, $S(O)_qR^{11}$, $OCONR^{12}R^{13}$, $NR^{14}R^{15}$, $NR^{16}COR^{17}$, $NR^{18}CONR^{19}R^{20}$, $SO_2NR^{21}R^{22}$, $NR^{23}SO_2R^{24}$, $CONR^{25}R^{26}$, $COR^{27}$, $CO_2R^{28}$, $OCOR^{29}$, $NR^{30}CO_2R^{31}$, $C_{1-6}$ alkyl (itself optionally substituted with halo, $C_{1-6}$ alkoxy, $C_{3-10}$ cycloalkyl, $CO_2(C_{1-6}$ alkyl), OCO $(C_{1-6}$ alkyl), $SO_2R^{32}$, $CONR^{33}R^{34}$, phenyl, phenoxy, heterocyclyl or heterocyclyloxy), $C_{3-10}$ cycloalkyl, $C_{1-6}$ alkoxy, $C_{1-6}$ haloalkoxy, $C_{2-6}$ alkenyl, $C_{2-6}$ alkynyl, methylenedioxy, phenyl, phenoxy, phenylthio, phenyl($C_{1-4}$) alkoxy, heterocyclyl, heterocyclyloxy or heterocyclyl $(C_{1-4})$alkoxy; wherein any of the immediately foregoing phenyl and heterocyclyl moieties are optionally substituted with halo, hydroxy, nitro, $S(O)_kC_{1-4}$ alkyl, $SO_2NH_2$, cyano, $C_{1-4}$ alkyl, $C_{1-4}$ aloxy, $CONH_2$, $CONH(C_{1-4}$ alkyl), $CO_2H$, $CO_2(C_{1-4}$ alkyl), $NHCO(C_{1-4}$ alkyl), $NHSO_2(C_{1-4}$ alkyl), $CO(CO_{1-4}$ alkyl), $CF_3$ or $OCF_3$;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{26}$, $R^{27}$, $R^{28}$, $R^{29}$, $R^{30}$, $R^{31}$, $R^{33}$ and $R^{34}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy);

$R^{11}$, $R^{24}$ and $R^{32}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy);

k and q are, independently, 0, 1 or 2;

or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, hydrobromide, phosphate, acetate, fumarate, maleate, tartrate, citrate, oxalate, methanesulphonate or p-toluenesulphonate.

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl or tert-butyl.

Alkenyl group are, for example, vinyl or allyl.

Cycloalkyl is mono-, bi or tricyclic and is, for example, cyclopropyl, cyclopentyl, cyclohexyl, norbornyl, bicyclo [2.2.1]heptyl or camphoryl.

Cycloalkenyl is especially monocyclic and is, for example, cyclopentenyl or cyclohexenyl.

Aryl is preferably phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Alternatively, heterocyclyl is an aromatic or non-aromatic 5 or 6 membered ring, optionally fused to one or more other rings, comprising at least one heteroatom selected from the group comprising nitrogen, oxygen and sulphur.

Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b] furyl, benz[b]thienyl, 2,3-dihydrobenz[b]thienyl (for example in 1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl, 2,1,3-benzothiadiazolyl, benzofurazan, quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo [3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin-4-one-yl), a benzothiazinyl (for example in 4H-benzo[1,4]thiazin-3-one-yl), benzo[d]imidazo[2,1-b]thiazol-2-yl or dibenzothiophenyl. Such heterocyclyl groups can, where appropriate, be in the form of an N-oxide (such as pyridine-N-oxide), an S-oxide or an S-dioxide.

Alternatively heterocyclyl is, for example, furyl, thienyl, 2,1,3-benzothiadiazole, 2,1,3-benzoxadiazole, quinoxaline, dihydro-1-benzopyrylium (for example a coumarin, a chromene or a chromone), piperidine, morpholine, pyrrole, indole, indoline, isoindoline, quinoline, thiazole, pyrazole, isoxazole, imidazole, pyridine, benzofuryl, benzimidazole, pyrimidine or dibenzothiophene.

In one aspect T is C=O or $CR^7R^8$, wherein $R^7$ and $R^8$ are, independently, hydrogen or $C_{1-4}$ alkyl (such as methyl).

In another aspect n is 0 or 1.

In a further aspect m is 0.

In a still further aspect X is O.

In another aspect $R^1$ is phenyl substituted with one or more of fluorine, chlorine, $C_{1-4}$ alkyl (especially methyl) or $C_{1-4}$ alkoxy (especially methoxy).

In a further aspect $R^1$ is phenyl optionally substituted (for example with one, two or three) by halo (especially fluoro or chloro), $C_{1-4}$ alkyl (especially methyl) or $C_{1-4}$ alkoxy (especially methoxy). In a still further aspect $R^1$ is phenyl substituted by one, two or three of: fluoro, chloro, methyl or methoxy.

In yet another aspect $R^1$ is phenyl optionally substituted by halogen (for example fluoro or chloro). The variable $R^1$ is, for example, 3,4-difluorophenyl or 3,4-dichlorophenyl.

In a still further aspect $R^2$ and $R^3$ are both hydrogen.

In another aspect $R^4$ is hydrogen or $C_{1-4}$ alkyl (such as methyl).

In yet another aspect $R^9$ is hydrogen, $C_{1-4}$ alkyl (such as methyl or iso-propyl) or phenyl($C_{1-4}$ alkyl) (such as benzyl).

In a still further aspect $R^{10}$ is hydrogen.

In yet another aspect $R^5$ is $C_{1-6}$ alkyl {optionally substituted by phenyl (itself optionally substituted by halogen or nitro), $CO_2(C_{1-4}$ alkyl), $C_{3-10}$ cycloalkyl (itself optionally substituted by oxo or $C_{1-4}$ alkyl) or heterocyclyl}, aryl (such as phenyl or naphthyl) {optionally substituted by halogen, $C_{1-6}$ alkyl, $C_{1-4}$ alkoxy, OH, nitro, cyano, $CF_3$, $OCF_3$, $N(C_{1-4}$ alkyl)$_2$, $NHCO(C_{1-4}$ alkyl), $CO_2H$ or $CO_2(C_{1-4}$ alkyl)} or hererocyclyl (such as thienyl, chromenyl, indolinyl, isoindolinyl, thiazolyl, quinolinyl, pyrazolyl, isoxazolyl or imidazolyl) {optionally substituted by halogen, oxo, $C_{1-4}$ alkyl, NHCO($C_{1-4}$ alkyl), CO($C_{1-4}$ alkyl), $CO_2H$, $CO_2$($C_{1-4}$ alkyl), pyridyl or isoxazolyl}.

In yet another aspect the present invention provides a compound of formula (Ia):

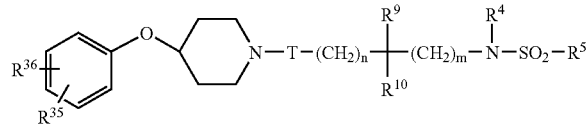

(Ia)

wherein:

T, n, m, $R^4$, $R^5$, $R^9$ and $R^{10}$ are as defined above;

$R^{35}$ is hydrogen, halogen or phenyl (optionally substituted by one or two halogen atoms or by one $CONR^{37}R^{38}$, $NR^{38}COR^{40}$, $SO_2R^{41}$, $SO_2NR^{42}R^{43}$ or $NR^{44}SO_2R^{45}$ group);

$R^{36}$ is hydrogen or halogen;

$R^{37}$, $R^{38}$, $R^{39}$, $R^{40}$, $R^{42}$, $R^{43}$ and $R^{44}$ are, independently, hydrogen, $C_{1-6}$ alkyl or aryl (itself optionally substituted by halo, $C_{1-6}$ alky, $C_{1-6}$ haloalkyl, CN, $NO_2$, $C_{1-6}$ alkoxy or $C_{1-6}$ haloalkoxy);

$R^{41}$ and $R^{45}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy);

or a pharmaceutically acceptable salt thereof.

In another aspect $R^{35}$ and $R^{36}$ are both chlorine or both fluorine, especially 3,4 disposed on the phenyl ring to which they are attached.

In a further aspect the present invention provides a compound of formula (Ib):

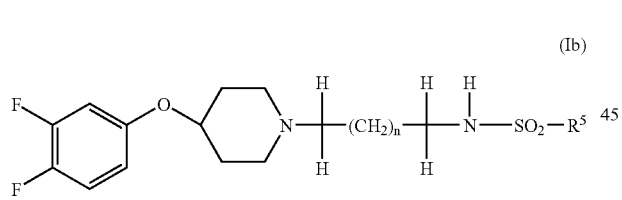

(Ib)

wherein n and $R^5$ are as defined above.

In a still further aspect the present invention provides a compound of formula (Ic):

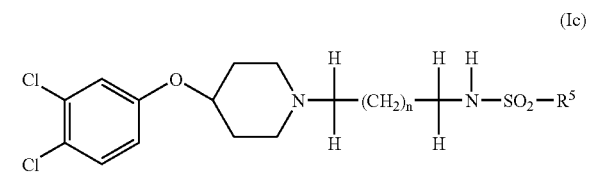

(Ic)

wherein n and $R^5$ are as defined above.

In another aspect the present invention provides a compound of formula (Id):

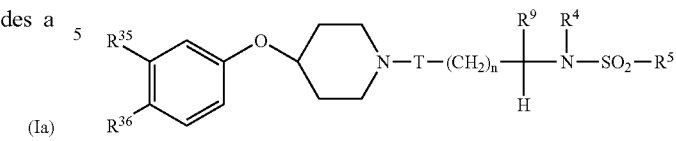

(Id)

wherein T, n, $R^4$, $R^5$, $R^9$, $R^{35}$ and $R^{36}$ are as defined above. It is preferred that $R^{35}$ and $R^{36}$ are halogen (for example fluoro or chloro).

In a further aspect the present invention provides a compound of formula (Ie):

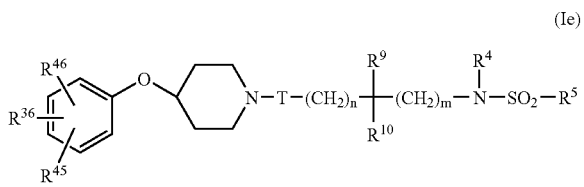

(Ie)

wherein T, n, m, $R^4$, $R^5$, $R^9$ and $R^{10}$ are as defined above; and $R^{35}$, $R^{36}$ and $R^{46}$ are, independently, hydrogen, halogen (especially fluoro or chloro), $C_{1-4}$ alkyl (especially methyl) or $C_{1-4}$ alkoxy (especially methoxy). In a still further aspect $R^{35}$, $R^{36}$ and $R^{46}$ are, independently, hydrogen, fluoro, chloro, methyl or methoxy, but not all hydrogen.

A compound of formula (I) can be prepared by coupling a compound of formula (II):

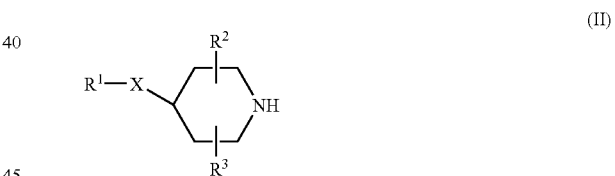

(II)

with a compound of formula (III):

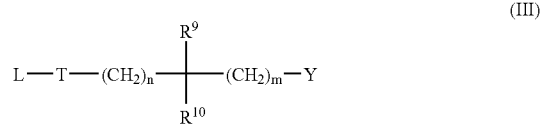

(III)

wherein L is a suitable leaving group, when Y is $NR^4S(O)_2$ $R^5$ then $R^4$ is not hydrogen, when Y is $S(O)_2NR^4R^5$ then neither $R^4$ nor $R^5$ is hydrogen and T is optionally protected during the course of the reaction by a standard protecting group known in the art and deprotected in a separate step or during the reaction work-up. For example:

when T is carbonyl, L can be OH and the coupling can be carried out in the presence of a coupling agent (such as bromo-tris-pyrrolidino-phosphonium hexafluorophosphate, PYBROP™); or, when T is $CR^7R^8$, L can be chloro or bromo and the coupling can be carrier out in the presence of a suitable base (such as potassium carbonate) in a suitable solvent (such as acetone).

A compound of formula (II) can be prepared by deprotecting a compound of formula (IV):

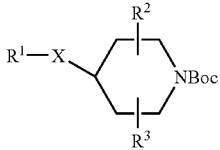
(IV)

wherein Boc is tert-butoxycarbonyl, for example using trifluoroacetic acid in a suitable solvent (such as dichloromethane) or using a source of hydrogen chloride in a suitable solvent (such as dioxane).

Alternatively, a compound of formula (I), wherein Y is $NR^4S(O)_2R^5$, can be prepared by reacting a compound of formula (V):

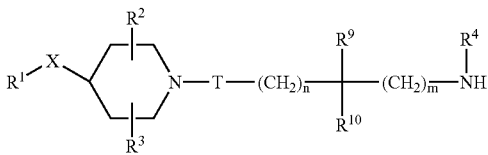
(V)

with a suitable sulphonyl chloride $ClSO_2R^5$.

A compound of formula (V) can be prepared by deprotecting the corresponding carbamate or 1H-isoindole-1,3 (2H)-dione. The corresponding carbamate or 1H-isoindole-1,3(2H)-dione can be prepared by reacting a compound of formula (II) with a compound of formula (VI) or (VII):

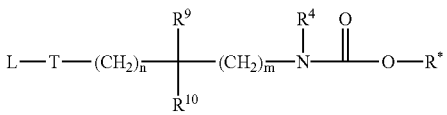
(VI)

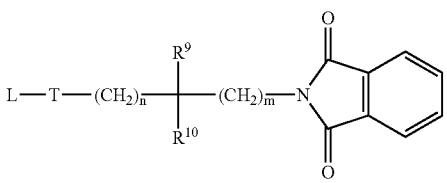
(VII)

wherein R* is, for example, $C_{1-6}$ alkyl; and L is as defined above.

A compound of formula (I) wherein m and n are both 0, T is $CH_2$, $R^9$ and $R^{10}$ are both hydrogen and Y is $S(O)_2NR^4R^5$, can be prepared by reacting a compound of formula (II) with a compound of formula (IX):

(IX)

in a suitable solvent (such as an aliphatic alcohol, for example methanol).

Compounds of formula (II), (III), (IV), (VI), (VII) and (IX) can be prepared by or adapting either methods described in the art or methods described in the Examples.

In another aspect the present invention provides processes, as described herein, for the preparation of compounds of formula (I), (I'), (Ia), (Ib), (Ic), (Id) and (Ie).

The intermediates of formula (V) are provided as a further feature of the invention.

Examples of compounds of formula (Ib) are listed in Table I below.

TABLE I (Ib)

| Compound | n | $R^5$ | M + H |
|---|---|---|---|
| 1 | 0 | 2-OCF$_3$—C$_6$H$_4$ | 481 |
| 2 | 0 | 3-NO$_2$-4-OH—C$_6$H$_3$ | 476 |
| 3 | 0 | (7,7-dimethyl-2-oxobicyclo[2.2.1]hept-1-yl)CH$_2$ | 471 |
| 4 | 0 | n-Propyl | 363 |
| 5 | 0 | C$_6$(CH$_3$)$_5$ | 467 |
| 6 | 0 | 4-n-propyl-C$_6$H$_4$ | 439 |
| 7 | 0 | Naphth-2-yl | 447 |
| 8 | 0 | 2,6-Cl$_2$—C$_6$H$_3$ | 465 |
| 9 | 0 | 2,6-F$_2$—C$_6$H$_3$ | 433 |
| 10 | 0 | 4-NO$_2$—C$_6$H$_4$ | 442 |
| 11 | 0 | 2,5-Cl$_2$—C$_6$H$_3$ | 465 |
| 12 | 0 | 5-(NMe$_2$)-naphth-1-yl | 490 |
| 13 | 0 | 2,1,3-benzothiadiazol-4-yl | 455 |
| 14 | 0 | 4-ethyl-C$_6$H$_4$ | 425 |
| 15 | 0 | 2,5-Cl$_2$-thien-3-yl | 471 |
| 16 | 0 | 3,4-(OMe)$_2$—C$_6$H$_3$ | 457 |
| 17 | 0 | 2-Cl-5-CF$_3$—C$_6$H$_3$ | 499 |
| 18 | 0 | 5-Cl-thien-2-yl | 437 |
| 19 | 0 | 4-Cl—C$_6$H$_4$ | 431 |
| 20 | 0 | 4-iso-propyl-C$_6$H$_4$ | 439 |
| 21 | 0 | 2-Cl-4-CF$_3$—C$_6$H$_3$ | 499 |
| 22 | 0 | 2,1,3-benzoxadiazol-4-yl | 439 |
| 23 | 0 | 3-methyl-C$_6$H$_4$ | 411 |
| 24 | 0 | iso-propyl | 363 |
| 25 | 0 | 4-CO$_2$H—C$_6$H$_4$ | 441 |
| 26 | 0 | 2-oxo-2H-chromen-6-yl | 465 |
| 27 | 0 | 3,4-Cl$_2$—C$_6$H$_3$ | 465 |
| 28 | 0 | 2,3-Cl$_2$—C$_6$H$_3$ | 465 |
| 29 | 0 | (2-NO$_2$—C$_6$H$_4$)CH$_2$ | 456 |
| 30 | 0 | 3-CF$_3$—C$_6$H$_4$ | 465 |
| 31 | 0 | 4-tert-butyl-C$_6$H$_4$ | 453 |
| 32 | 0 | 2-NO$_2$—C$_6$H$_4$ | 442 |
| 33 | 0 | 2-F—C$_6$H$_4$ | 415 |
| 34 | 0 | 3-NO$_2$—C$_6$H$_4$ | 442 |
| 35 | 0 | 1-acetyl-indolin-5-yl | 480 |
| 36 | 0 | Naphth-1-yl | 447 |
| 37 | 0 | 2-OMe-5-Cl—C$_6$H$_3$ | 461 |
| 38 | 0 | 3-F—C$_6$H$_4$ | 415 |
| 39 | 0 | 3-Cl-4-(NHCOCH$_3$)—C$_6$H$_3$ | 488 |
| 40 | 0 | Benzyl | 411 |
| 41 | 0 | 2-NO$_2$-4-OMe—C$_6$H$_3$ | 472 |
| 42 | 0 | 2-Me-5-NO$_2$—C$_6$H$_3$ | 456 |
| 43 | 0 | 3-CO$_2$H—C$_6$H$_4$ | 441 |

TABLE I-continued

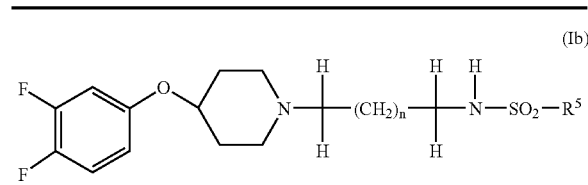

(Ib)

| Compound | n | R⁵ | M + H |
|---|---|---|---|
| 44 | 0 | 2,4,6-Me₃—C₆H₂ | 439 |
| 45 | 0 | 3,4-Cl₂—C₆H₃ | 465 |
| 46 | 0 | 4-(NHCOCH₃)—C₆H₄ | 454 |
| 47 | 0 | 2-CF₃—C₆H₄ | 465 |
| 48 | 0 | (CH₂)₂CO₂CH₃ | 407 |
| 49 | 0 | 4-CH₃—C₆H₄ | 411 |
| 50 | 0 | 4-CF₃—C₆H₄ | 465 |
| 51 | 0 | 4-CN—C₆H₄ | 422 |
| 52 | 0 | 3-NO₂-4-CH₃—C₆H₃ | 456 |
| 53 | 0 | 2-(NHCOCH₃)-4-CH₃-thiazol-5-yl | 475 |
| 54 | 0 | Quinolin-8-yl | 448 |
| 55 | 0 | 2-OH-3,5-Cl₂—C₆H₂ | 481 |
| 56 | 0 | 2,5-(OMe)₂—C₆H₃ | 457 |
| 57 | 0 | Phenyl | 397 |
| 58 | 0 | 2-CH₃-4-NO₂—C₆H₅ | 456 |
| 59 | 0 | 5-(pyrid-2-yl)-thien-2-yl | 480 |
| 60 | 0 | 1,3-(CH₃)₂-5-Cl-pyrazol-4-yl | 449 |
| 61 | 0 | 3,5-(CH₃)₂-isoxazol-4-yl | 416 |
| 62 | 0 | 2,3,6-(CH₃)₃-4-OMe—C₆H | 469 |
| 63 | 0 | 1-CH₃-imidazol-4-yl | 401 |
| 64 | 0 | 2-OMe-5-Me—C₆H₃ | 441 |
| 65 | 0 | 5-(isoxazol-3-yl)-thien-2-yl | 470 |
| 66 | 0 | 2-(CO₂CH₃)-thien-3-yl | 461 |
| 67 | 0 | 4-tert-pentyl-C₆H₄ | 467 |

TABLE I-continued

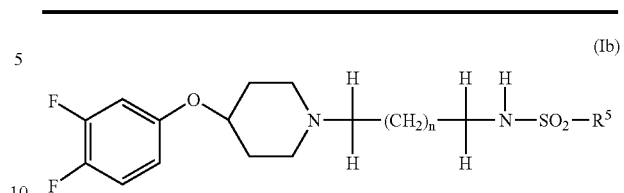

(Ib)

| Compound | n | R⁵ | M + H |
|---|---|---|---|
| 68 | 0 | 1-(1,3-dioxo-1,3-dihydro-2H-isoindol-2-yl)-eth-1-yl | 494 |
| 69 | 1 | 5-(pyridin-2-yl)-thien-2-yl | |

TABLE II

Table II comprises 69 compounds of formula (Ic):

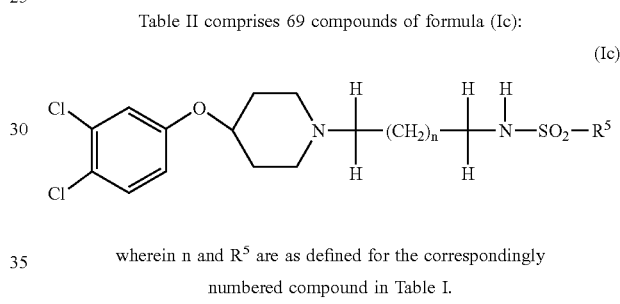

(Ic)

wherein n and R⁵ are as defined for the correspondingly numbered compound in Table I.

TABLE III

Table III discloses compounds of formula (Id):

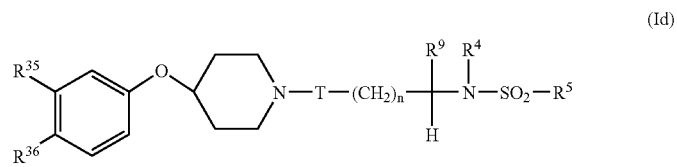

(Id)

wherein the variables are defined in the Table below.

| Compound | R³⁵ | R³⁶ | T | n | R⁹ | R⁴ | R⁵ |
|---|---|---|---|---|---|---|---|
| 1 | Cl | Cl | CH₂ | 1 | H | H | 2-(pyridin-2-yl)thien-5-yl |
| 2 | F | F | C=O | 0 | (S)-benzyl | H | 2-(pyridin-2-yl)thien-5-yl |
| 3 | F | F | CH₂ | 0 | (S)-benzyl | H | 2-(pyridin-2-yl)thien-5-yl |
| 4 | Cl | Cl | CH₂ | 0 | (S)-iso-propyl | H | 2-(pyridin-2-yl)thien-5-yl |
| 5 | Cl | Cl | CH₂ | 0 | (S)-iso-propyl | H | 2,5-(OCH₃)₂—C₆H₃ |
| 6 | F | F | C(CH₃)₂ | 0 | H | H | 2-(pyridin-2-yl)thien-5-yl |
| 7 | F | F | CHCH₃ | 0 | H | H | 2-(pyridin-2-yl)thien-5-yl |
| 8 | F | F | CH₂ | 0 | H | CH₃ | 2-(pyridin-2-yl)thien-5-yl |

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)). Examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

According to a further feature of the invention there is provided a compound of the formula (I), (I'), (Ia), (Ib), (Ic), (Id) or (Ie) or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity) in a warm blooded animal, such as man, in need of such treatment, which comprises administering to said animal an effective amount of a compound of the present invention, or a pharmaceutically acceptable salt thereof or a solvate thereof.

The invention also provides a compound of the formula (I), (I'), (Ia), (Ib), (Ic), (Id) or (Ie) or a pharmaceutically acceptable salt thereof or a solvate thereof, for use as a medicament.

In another aspect the present invention provides the use of a compound of the formula (I), (I'), (Ia), (Ib), (Ic), (Id) or (Ie) or a pharmaceutically acceptable salt thereof or a solvate thereof, in the manufacture of a medicament for use in therapy (for example modulating chemokine receptor activity (especially CCR3 receptor activity) in a warm blooded animal, such as man).

The invention further provides the use of a compound of formula (I), (I'), (Ia), (Ib), (Ic), (Id) or (Ie) or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a warm blooded animal, such as man.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I), (I'), (Ia), (Ib), (Ic), (Id) or (Ie) or a pharmaceutically acceptable salt thereof or solvate thereof.

In a further aspect a compound of formula (I), (I'), (Ia), (Ib), (Ic), (Id) or (Ie), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I), (I'), (Ia), (Ib), (Ic), (Id) or (Ie), or a pharmaceutically acceptable salt thereof, is useful in the treatment of asthma.

The present invention also provides a the use of a compound of formula (I), (I'), (Ia), (Ib), (Ic), (Id) or (Ie), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I), (I'), (Ia), (Ib), (Ic), (Id) or (Ie), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity, said ingredient is normally formulated in accordance with standard pharmaceutical practice as a pharmaceutical composition.

Therefore in another aspect the present invention provides a pharmaceutical composition which comprises a compound of the formula (I), (I'), (Ia), (Ib), (Ic), (Id) or (Ie) or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), (I'), (Ia), (Ib), (Ic), (Id) or (Ie) or a pharmaceutically-acceptable salt thereof (hereafter Compound X), for therapeutic or prophylactic use in humans:

| (a) | |
|---|---|
| Tablet I | mg/tablet |
| Compound X | 100 |
| Lactose Ph. Eur. | 179 |
| Croscarmellose sodium | 12.0 |
| Polyvinylpyrrolidone | 6 |
| Magnesium stearate | 3.0 |

| (b) | |
|---|---|
| Tablet II | mg/tablet |
| Compound X | 50 |
| Lactose Ph. Eur. | 229 |
| Croscarmellose sodium | 12.0 |
| Polyvinylpyrrolidone | 6 |
| Magnesium stearate | 3.0 |

| (c) | |
|---|---|
| Tablet III | mg/tablet |
| Compound X | 1.0 |
| Lactose Ph. Eur. | 92 |
| Croscarmellose sodium | 4.0 |
| Polyvinylpyrrolidone | 2.0 |
| Magnesium stearate | 1.0 |

| (d) | |
|---|---|
| Capsule | mg/capsule |
| Compound X | 10 |
| Lactose Ph. Eur. | 389 |
| Croscarmeflose sodium | 100 |
| Magnesium stearate | 1.0 |

| (e) | |
|---|---|
| Injection I | (50 mg/ml) |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limiting examples in which, unless stated otherwise:
(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO ($CD_3SOCD_3$) or $CDCl_3$ as the solvent unless otherwise stated;
(ii) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the positive mass ion—$(M+H)^+$;
(iii) the following abbreviations are used:
  THF=tetrahydrofuran
  DMF=N,N-dimethylformamide
  HPLC=high pressure liquid chromatography
  BOC=tert-butoxycarbonyl
  TEA=triethylamine
(iv) the title and sub-titled compounds of the examples and methods were named using the ACD/name program from Advanced Chemical Development Inc, Canada;
(v) unless stated otherwise, reverse phase HPLC was conducted using a Symmetry, NovaPak or Ex-Terra reverse phase silica column; and
(vi) solvents were dried with $MgSO_4$ or $Na_2SO_4$.

EXAMPLE 1

This Example illustrates the preparation of 4-(3,4-dichlorophenoxy)piperidine.

Step a: tert-Butyl 4-(3,4-dichlorophenoxy)-1-piperidinecarboxylate

Diethyl azodicarboxylate (41.0 ml) was added to a solution of triphenylphosphine (62.9 g) in tetrahydrofuran (800 ml) at 0° C. After 15 minutes 3,4-dichlorophenol (39.1 g) was added, after a further 15 minutes tert-butyl 4-hydroxy-1-piperidinecarboxylate (48.3 g) in tetrahydrofuran (400 ml) was added dropwise over 30 min. The solution was stirred at room temperature for 16 hours and concentrated to a small volume. Purification by flash silica chromatography (ethyl acetate:iso-hexane 95:5) gave the sub-title compound as an oil (61.3 g).
MS: APCI(+ve): 246 (M–BOC+2H)

Step b: 4-(3,4-Dichlorophenoxy)piperidine

The product from Example 1, step a) was dissolved in dichloromethane (600 ml) and trifluoroacetic acid (300 ml) was added. After 24 hours at room temperature the solution was evaporated and the resultant gum triturated under ether to give the sub-titled product as a solid (36.6 g). The free base was liberated by addition of aqueous NaOH (2M) and extraction with ethyl acetate followed by evaporation of solvent to give the title compound as a gum (25 g).
$^1$H NMR: δ($CDCl_3$) 1.77 (1H, br s), 2.05–2.26 (4H, m), 3.20–3.49 (4H, m), 4.61 (1H, s), 6.69–7.52 (3H, m).

EXAMPLE 2

This Example illustrates the preparation of N-{3-[4-(3,4-dichlorophenoxy)piperidin-1-yl]propyl}-5-pyridin-2-ylthiophene-2-sulfonamide (Compound 1 of Table III).

Step a: tert-Butyl 3-[4-(3,4-dichlorophenoxy)-1-piperidinyl]propylcarbamate

The product from Example 1 Step (b) (10 g) was dissolved in DMF (50 ml) and triethylamine (14.8 ml) was added. tert-Butyl 3-bromopropylcarbamate (10 g) was then added and the solution stirred at room temperature for 24 hrs. The solvent was evaporated and the resulting solid dissolved in ethyl acetate and water were added, the organic phase separated, dried, filtered and evaporated to a solid (17.51 g).
MS: ESI (+ve): 403 (M+H)

Step b: 3-[4-(3,4-dichlorophenoxy)-1-piperidinyl]propylamine

The product from Example 2 Step (a) (2 g) was dissolved in dioxan (100 ml) and 6N HCl (100 ml) added. After 18 hrs at room temperature the solvent was evaporated and the resultant solid basified with NaOH (2M) to pH 11. The aqueous was extracted with ethyl acetate, the organic phase separated, dried, filtered and evaporated to leave the sub-title compound as an oil (1.1 g).
MS: ESI (+ve): 303 (M+H)

Step c: N-{3-[4-(3,4-dichlorophenoxy)piperidin-1-yl]propyl}-5-pyridin-2-ylthiophene-2-sulfonamide The product of Example 2, Step (b) (0.2 g) was dissolved in acetone (4 ml). Potassium carbonate [0.130 g dissolved in $H_2O$ (1 ml)] was then added, followed by 5-pyridin-2-yl-thiophene-2-sulfonyl chloride (0.171 g) and the reaction left to stir for 10 mins. Water was then added and the product extracted with ethyl acetate. The combined organic extracts dried, filtered and concentrated. Purification by reverse phase HPLC {with a gradient eluent system [30% MeCN/$NH_4OAc_{aq}$ (0.1%) to 95% MeCN//$NH_4OAc_{aq}$ (0.1%)]} gave the title compound as a solid (0.135 g).
$^1$H NMR: δ ($CDCl_3$) 1.72 (2H, quintet), 1.84–1.91 (2H, m), 1.98–2.04 (2H, m), 2.39–2.47 (2H, m), 2.52 (2H, t), 2.62–2.71 (2H, m), 3.23 (2H, t), 4.32–4.38 (1H, m), 6.75 (1H, dd), 6.99 (1H, d), 7.23 (1H, d), 7.25 (1H, dd), 7.32(1H, d), 7.49 (1H, d), 7.57 (1H, d), 7.75 (1H, dt), 8.59 (1H, ddd).
Melting point: 115° C.

EXAMPLE 3

This Example illustrates the preparation of N-{3-[4-(3,4-difluorophenoxy)-1-piperidinyl]propyl}-5-(2-pyridinyl)-2-thiophenesulfonamide (Compound 69 in Table I).

Step a: tert-Butyl 4-(3,4-difluorophenoxy)-1-piperidinecarboxylate

The sub-title compound was prepared according to the method of Example 1, step (a) using 3,4-difluorophenol to afford an oil (5.4 g).
MS: ESI (+ve): 213 (M–BOC+H)

Step b: 4-(3,4-Difluorophenoxy)piperidine

The sub-title compound was prepared according to the method of Example 1, step (b) to afford a pale yellow oil (3 g).
MS: ESI (+ve): 214 (M+H)

Step c: 2-{3-[4-(3,4-difluorophenoxy)-1-piperidinyl]propyl}-1H-isoindole-1,3(2H)-dione The product from Example 3, Step (b) (1.5 g) was dissolved in CH$_2$Cl$_2$ (26 ml) and triethylamine (1.18 ml) was added. 2-(3-Bromopropyl)-1H-isoindole-1,3(2H)-dione (2.08 g) was then added and the solution stirred at room temperature for 12 hrs. Ethyl acetate and aqueous NaHCO$_3$ solution were added and product was extracted with ethyl acetate. The combined organic extracts were dried, filtered and concentrated. This gave the sub-titled product as a solid (1.55 g).

MS: APCI(+ve): 401 (M+H)

Step d: 3-[4-(3,4-difluorophenoxy)-1-piperidinyl]propylamine

To the product of Example 3, Step (c) in EtOH (30 ml) was added hydrazine monohydrate (0.562 ml). The reaction was refluxed for 4 hrs and the solvent evaporated. Dichloromethane (40 ml) was added and the solid by-product filtered. The organic residue was evaporated and the product purified by reverse phase HPLC {with a gradient eluent system [25% MeCN/NH$_4$OAc$_{aq}$ (0.1%) to 95% MeCN// NH$_4$OAc$_{aq}$ (0.1%)]} to give the sub-title compound as a solid (0.622 g).

$^1$H NMR: δ(CDCl$_3$) 1.80–1.86 (4H, m) 1.95–2.02 (2H, m), 2.46 (2H, br s), 2.61 (2H, t), 2.75 (2H, br s), 3.04 (2H, t), 4.26 (1H, br s), 6.56–7.27 (5H, m).

Step e: N-{3-[4-(3,4-difluorophenoxy)-1-piperidinyl]propyl}-5-(2-pyridinyl)-2-thiophenesulfonamide The product of Example 3, Step (d) (0.3 g) was dissolved in pyridine (1 ml) and CH$_2$Cl$_2$ (4 ml). 5-Pyridin-2-yl-thiophene-2-sulfonyl chloride (0.317 g) [dissolved in CH$_2$Cl$_2$ (4 ml)] was then added and the reaction left to stir for 1 hr. The reaction mixture was poured onto flash silica and the silica flushed with 5% MeOH/94% CH$_2$Cl$_2$/1% aq NH$_3$ as eluent. Evaporation of solvent and purification using reverse phase HPLC {with a gradient eluent system [25% MeCN/NH$_4$OAc$_{aq}$ (0.1%) to 95% MeCN//NH$_4$OAc$_{aq}$ (0.1%)]} gave the title compound as a solid (0.120 g).

$^1$H NMR: δ(DMSO) 1.50–1.90 (6H, m), 2.07–2.14 (2H, m), 2.27 (2H, t), 2.55–2.61 (2H, m), 2.93 (2H, t), 4.26–4.35 (1H, m), 6.71–8.58 (9H, m)

Melting point: 128–129° C.

EXAMPLE 4

This Example illustrates the preparation of N-{2-[4-(3,4-difluorophenoxy)-1-piperidinyl]ethyl}-5-(2-pyridinyl)-2-thiophenesulfonamide (Compound 59 of Table I).

Step a: tert-Butyl 2-[4-(3,4-difluorophenoxy)-1-piperidinyl]ethylcarbamate

The product from Example 3, Step (b) (5 g) was dissolved in DMF (27 ml) and triethylamine (7.7 ml) was added. tert-Butyl 2-bromoethylcarbamate (5.8 g) was added and the solution stirred at room temperature for 24 hrs. The solvent was evaporated and the residue dissolved in ethyl acetate and washed with water. The organic phase separated, dried, filtered and evaporated. Purification by flash silica chromatography (dichloromethane:methanol 97:3) gave the sub-titled product as an oil (10 g) containing a small amount of DMF.

MS: APCI(+ve): 357 (M+H)

Step b: 2-[4-(3,4-difluorophenoxy)-1-piperidinyl]ethylamine

The product of Example 4, Step (a) (10 g) was dissolved in dioxane (114 ml) and HCl (6N) (114 ml) was added and the reaction stirred for 2 hrs. The organic solvent was evaporated and aqueous NaOH (2M) added. The product was extracted with ethyl acetate, the combined organic extracts dried, filtered and concentrated to give the sub-title product as an oil (4.65 g).

$^1$H NMR: δ(CDCl$_3$) 1.74–1.83 (2H, m), 1.95–2.00 (2H, m), 2.26–2.31 (2H, m), 2.43 (2H, t), 2.73 (2H, br s), 2.79 (2H, t), 4.17–4.23 (1H, m), 6.58–7.07 (3H, m).

MS: APCI(+ve): 257 (M+H)

Step c: N-{2-[4-(3,4-difluorophenoxy)-1-piperidinyl]ethyl}-5-(2-pyridinyl)-2-thiophenesulfonamide To a solution of 5-pyridin-2-yl-thiophene-2-sulfonyl chloride (0.213 g) [in CH$_2$Cl$_2$ (10 ml)] was added a solution of the product of Example 4, Step (b) (0.210 g) [in CH$_2$Cl$_2$ (5 ml) and pyridine (0.066 ml)]. The reaction was left to stir for 12 hrs. The reaction mixture was washed with saturated aqueous NaCl solution and the organics separated and dried and then filtered. The solvents were evaporated and the product purified by using reverse phase HPLC {with a gradient eluent system [25% MeCN/NH$_4$OAc$_{aq}$ (0.1%) to 95% MeCN//NH$_4$OAc$_{aq}$ (0.1%)]} give the title compound as a solid (0.03 g).

$^1$H NMR: δ (CDCl$_3$) 1.69–1.79 (2H, m), 1.86–1.92 (2H, m), 2.22–2.26 (2H, m), 2.51 (2H, t), 2.53–2.60 (2H, m), 3.15 (2H, t), 4.15–4.24 (1H, m), 6.55–6.57 (1H, m), 6.66–6.70 (1H, m), 7.03 (1H, q), 7.24–7.27 (1H, m), 7.49–7.51 (1H, m), 7.60–7.61 (1H, m), 7.68 (1H, d), 7.75 (1H, t), 8.59 (1H, d).

Melting point: 144–145° C.

EXAMPLE 5

This Example illustrates the preparation of N-{(1S)-1-benzyl-2-[4-(3,4-difluorophenoxy)-1-piperidinyl]-2-oxoethyl}-5-(2-pyridinyl)-2-thiophenesulfonamide (Compound 2 of Table III).

Step a: tert-Butyl (1S)-1-benzyl-2-[4-(3,4-difluorophenoxy)-1-piperidinyl]-2-oxoethylcarbamate The product of Example 3, Step (b) (1 g) was dissolved in CH$_2$Cl$_2$ (20 ml) and (2S)-2-[(tert-butoxycarbonyl)amino]-3-phenylpropanoic acid (1.24 g), N,N-di-iso-propylethylamine (2.45 ml) and PyBrop (bromo-tris-pyrrolidino-phosphonium hexafluorophosphate, 3.2 g) were added. After 1 hr at room temperature CH$_2$Cl$_2$ was added and the mixture washed with HCl (2N), aqueous NaHCO$_3$ solution, and saturated aqueous NaCl solution. The organic phase was dried, filtered and evaporated. Purification by flash silica chromatography (hexane:ethyl acetate 70:30) gave the sub-titled product as solid (1.6 g).

MS: ESI(+ve): 461 (M+H)

Step b: (1S)-1-Benzyl-2-[4-(3,4-difluorophenoxy)-1-piperidinyl]-2-oxoethylamine

The product from Example 5, Step (a) (1.2 g) was dissolved in dichloromethane (10 ml) and trifluoroacetic acid (5 ml) was added. After 1 hr at room temperature the solution was evaporated and aqueous NaOH (2M) added. The product was extracted with ethyl acetate, the combined organic extracts dried, filtered and concentrated to give the sub-title product as an oil (1 g).

MS: ESI(+ve): 361 (M+H)

Step c: N-{(1S)-1-benzyl-2-[4-(3,4-difluorophenoxy)-1-piperidinyl]-2-oxoethyl}-5-(2-pyridinyl)-2-thiophenesulfonamide To a solution of 5-pyridin-2-yl-thiophene-2-sulfonyl chloride (0.072 g) [in CH$_2$Cl$_2$ (5 ml) and dimethyl amino pyridine (0.034 g)] was added a solution of the product of Example 5, Step (b) (0.100 g) in CH$_2$Cl$_2$ (1 ml). The reaction was left to stir for 12 hrs. The reaction mixture was then pre-absorbed onto flash silica and purified by flash silica column chromatography with 2% MeOH/97.5% $CH_2Cl_2$/0.5% aq $NH_3$ as eluent. Further purification using flash silica chromatography with 10% MeCN/2% TEA/88% $CH_2Cl_2$ eluent gave the title compound as a solid (0.045 g).

$^1$H NMR: δ ($CDCl_3$) 1.23–1.73 (4H, m), 2.97 (2H, d), 2.93–3.55 (4H, m), 4.05–4.15 (1H, m), 4.55–4.60 (1H, m), 5.94 (1H, s), 6.31–8.57 (14H, m).

MS: APCI(+ve): 584 (M+H).

EXAMPLE 6

This Example illustrates the preparation of N-{(1S)-1-benzyl-2-[4-(3,4-difluorophenoxy)-1-piperidinyl]ethyl}-5-(2-pyridinyl)-2-thiophenesulfonamide (Compound 3 of Table III).

Step a: (1S)-1-Benzyl-2-[4(3,4-difluorophenoxy)-1-piperidinyl]ethylamine

The product from Example 5, Step (b) (0.1 g) was dissolved in THF (3 ml) and borane [0.84 ml (1M in THF)] was added. The reaction was stirred for 1 hr and then quenched slowly with methanol. The solvents were evaporated and the residue re-dissolved in 50% $H_2O$/50% conc HCl (2 ml) and refluxed for 1 hr. The solvents were evaporated. The free base was liberated by addition of aqueous NaOH (2M) and extraction with ethyl acetate followed by drying, filtration and evaporation of solvent to give the sub-title compound as an oil (0.092 g).

MS: APCI(+ve): 347 (M+H)

Step b: N-{(1S)-1-benzyl-2-[4-(3,4-difluorophenoxy)- 1-piperidinyl]ethyl}-5-(2-pyridinyl)-2-thiophenesulfonamide The product of Example 6, Step (a) (0.091 g) was dissolved in acetone (2 ml). Potassium carbonate [0.066 g dissolved in $H_2O$ (0.5 ml)] was then added, followed by 5-pyridin-2-yl-thiophene-2-sulfonyl chloride (0.067 g) and the reaction left to stir for 10 mins. Water was then added and the product extracted with ethyl acetate. The combined organic extracts dried, filtered and concentrated. Purification by flash silica column chromatography with 1% MeOH/98.9% $CH_2Cl_2$/0.1% aq $NH_3$ as eluent, and then reverse phase HPLC {with a gradient eluent system [50% MeCN/$NH_4OAc_{aq}$ (0.1%) to 70% MeCN//$NH_4OAc_{aq}$ (0.1%)]} gave the title compound as a solid (0.057 g).

$^1$H NMR: δ ($CDCl_3$) 1.61 (2H, m), 1.71–1.81 (2H, m), 2.00–2.09 (2H, m), 2.20–2.26 (2H, m), 2.30–2.38 (2H, m), 2.82–2.88 (1H, dd), 3.24–3.29 (1H, dd), 3.45–3.51 (1H, m), 4.08 (1H, m), 6.47–6.50 (1H, m), 6.62 (1H, m), 6.95 (1H, q), 7.19–7.30 (6H, m), 7.50–7.51 (1H, m), 7.61–7.62 (1H, m), 7.66 (1H, d), 7.74 (1H, t), 8.58 (1H, m).

MS: APCI(+ve): 570 (M+H)

EXAMPLE 7

This Example illustrates the preparation of N-((1S)-1-{[4-(3,4-dichlorophenoxy)-1-piperidinyl]methyl}-2-methylpropyl)-5-(2-pyridinyl)-2-thiophenesulfonamide (Compound 4 of Table III).

Step a: tert-Butyl (1S)-1-{[4-(3,4-dichlorophenoxy)-1-piperidinyl]carbonyl}-2-methylpropylcarbamate To (2S)-2-[(tert-butoxycarbonyl)amino]-3-methylbutanoic acid (1.13 g) in $CH_2Cl_2$ (5 ml) was added 1-ethyl-3-[3-(dimethylamino)-propyl]carbodiimide hydrochloride (0.99 g) and left to stir for 5 mins. The product of Example 1, Step (b) (0.98 g) dissolved in $CH_2Cl_2$ (5 ml) was then and the reaction left to stir for 3 hrs. Aqueous $NaHCO_3$ solution was added and the product extracted with ethyl acetate. The organic phase was dried, filtered and evaporated to give the sub-title compound (1.57 g).

MS: APCI(+ve): 345(M−BOC+H)

Step b: (1S)-1-{[4-(3,4-dichlorophenoxy)piperidin-1-yl]carbonyl}-2-methylpropylamine The product from Example 7, Step (a) (1.57 g) was dissolved in dichloromethane (14 ml) and trifluoroacetic acid (4 ml) was added. After 2 hours at room temperature the solution was evaporated and aqueous NaOH (2M) was added. The product was extracted with ethyl acetate, the combined organic extracts dried, filtered and concentrated to give the sub-title product as an oil (1.12 g).

MS: APCI(+ve): 345 (M+H)

Step c: (1S)-1-{[4-(3,4-Dichlorophenoxy)-1-piperidinyl]methyl}-2-methylpropylamine The product from Example 7, Step (b) (1.12 g) was dissolved in THF (10 ml) and borane [22.7 ml (1M in THF)] was added. The reaction was stirred for 2 hr and the solvents evaporated. The reaction was quenched slowly with MeOH followed by aqueous HCl (5 ml Concentrated HCl: 5 ml $H_2O$). The MeOH was evaporated and NaOH (2M) added until pH 9 was reached. The product was extracted with ethyl acetate and the combined organic extracts were washed with saturated aqueous $NaHCO_3$, dried, filtered and solvents evaporated to give the sub-title compound as an oil (0.98 g).

MS: APCI(+ve): 331 (M+H)

Step d: N-((1S)-1-{[4-(3,4-dichlorophenoxy)-1-piperidinyl]methyl}-2-methylpropyl)-5-(2-pyridinyl)-2-thiophenesulfonamide.

The product of Example 7, Step (c) (0.050 g) was dissolved in acetone (1 ml). $K_2CO_3$ [0.033 g dissolved in $H_2O$ (0.5 ml)] was then added, followed by 5-pyridin-2-yl-thiophene-2-sulfonyl chloride (0.041 g) and the reaction left to stir for 1 hr. Water was then added and the product extracted with ethyl acetate. The combined organic extracts dried, filtered and concentrated. Purification by flash silica column chromatography with 30% EtOAc/68% Hexane/2% TEA as eluent, and then reverse phase HPLC [(50% MeCN/$NH_4OAc_{aq}$ (0.1%)] gave the title compound as a solid (0.023 g).

$^1$H NMR: δ ($CDCl_3$) 0.88–0.94 (7H, m), 1.60–1.71 (2H, m), 1.76–1.87 (2H, m), 2.17–2.27 (2H, m), 2.32–2.38 (2H, m), 2.43–2.47 (2H, m), 3.22–3.28 (1H, m), 4.15–4.22 (1H, m), 6.68 (1H, dt), 6.90–6.92 (1H, m), 7.23–7.29 (2H, m), 7.50 (1H, t), 7.59 (1H, t), 7.65–7.67 (1H, m), 7.71–7.75 (1H, m), 8.58 (1H, m).

MS: APCI(+ve): 554 (M+H)

EXAMPLE 8

This Example illustrates the preparation of N-((1S)-1-{[4-(3,4-dichlorophenoxy)-1-piperidinyl]methyl}-2-methylpropyl)-2,5-dimethoxybenzenesulfonamide (Compound 5 of Table III).

The product of Example 7, Step (b) (0.050 g) was dissolved in acetone (1 ml), $K_2CO_3$ [0.033 g dissolved in $H_2O$ (0.3 ml)] was then added, followed by 2,5-dimethoxybenzenesulfonyl chloride (0.039 g). The reaction left stirring for 30 mins. Water was then added and the product extracted with ethyl acetate. The combined organic extracts were dried, filtered and concentrated. Purification by flash silica column chromatography with 1% MeOH/98.9% CH$_2$Cl$_2$/0.1% aq NH$_3$ as eluent gave the title compound as a solid (0.072 g).

$^1$H NMR: δ (CDCl$_3$) 0.85–0.90 (6H, m), 1.48–1.72 (5H, m), 2.25 (4H, m), 2.48 (2H, m), 3.20 (1H, m), 3.81 (3H, s), 3.95 (3H, s), 4.14 (1H, m), 5.28 (1H, m), 6.70–6.95 (1H, m), 6.95–6.98 (2H, m), 7.04–7.07 (1H, m), 7.26–7.31 (1H, m), 7.44 (1H, m).

MS: APCI(+ve): 531 (M+H)

EXAMPLE 9

This Example illustrates the preparation of N-{2-[4-(3,4-difluorophenoxy)-1-piperidinyl]-2-methylpropyl}-5-(2-pyridinyl)-2-thiophenesulfonamide (Compound 6 of Table III).

Step a: 2-[4-(3,4-dichlorophenoxy)-1-piperidinyl]-2-methyl-1-propanamine

The product of Example 3, Step (b) (1.5 g) was dissolved in acetone (1 ml). After five minutes 2-hydroxy-2-methylpropanenitrile (0.64 ml) was added and the reaction left to stir for 12 hrs. The solvent was allowed to evaporate and then THF (10 ml) was added followed by LiAlH$_4$ (1M in THF, 20 ml) and the reaction left to stir overnight. The reaction was then quenched with H$_2$O (0.5 ml), followed by NaOH (15% solution in H$_2$O (0.5 ml) and then H$_2$O (1.5 ml). Ethyl acetate was then added and the mixture dried and filtered. The organics were evaporated and purification by flash silica column chromatography with 10% MeOH/90% CH$_2$Cl$_2$ as eluent gave the sub-title compound as an oil (0.60 g).

$^1$H NMR: δ (CDCl$_3$) 1.01 (6H, s), 1.45 (2H, br s), 1.69–1.79 (2H, m), 1.96–2.00 (2H, m), 2.30–2.40 (2H, m), 2.58 (2H, m), 2.79–2.81 (2H, m), 4.14–4.19 (1H, m), 6.56–7.09 (3H, m).

MS: ESI(+ve): 285 (M+H)

Step b: N-{2-[4-(3,4-difluorophenoxy)-1-piperidinyl]-2-methylpropyl}-5-(2-pyridinyl)-2-thiophenesulfonamide Prepared by the method of Example 7, Step (d) using the product of Example 9, Step (a) to give the title compound as a solid (0.137 g).

$^1$H NMR: δ (DMSO) 0.98 (6H, s), 1.51–1.59 (2H,m), 1.85–1.89 (2H, m), 2.24–2.33 (2H, m), 2.67–2.70 (2H, m), 2.86 (2H, s), 4.24–4.31 (1H, m), 6.71–8.58 (10H, m).

Melting point: 133–134° C.

EXAMPLE 10

This Example illustrates the preparation of N-{2-[4-(3,4-difluorophenoxy)-1-piperidinyl]propyl}-5-(2-pyridinyl)-2-thiophenesulfonamide (Compound 7 of Table III).

Step a: N-{2-[4-(3,4-difluorophenoxy)-1-piperidinyl]propyl}-2-phenylacetamide

The product of Example 3, Step (b) (0.8 g) was dissolved in 1,2-dichloroethane (14 ml). N-(2-oxopropyl)-2-phenylacetamide was added (0.72 g) followed by NaBH(OAc)$_3$ (1.12 g) and acetic acid (0.12 g). After 18 hours at room temperature aqueous NaOH (1M) solution and ethyl acetate were added. The product was extracted ethyl acetate, the combined organic extracts dried, filtered and concentrated. Purification by flash silica column chromatography (dichloromethane:methanol 95:5) gave the sub-title compound (0.77 g).

MS: APCI(+ve): 389 (M+H)

Step b: 2-[4-(3,4-Difluorophenoxy)-1-piperidinyl]-1-propanamine

To the product of Example 10, Step (a) (0.772 g) was added 50% conc HCl/50% MeOH (20 ml) and the reaction heated to 60° C. for 2 days. Evaporation of solvent and purification by flash silica column chromatography using 10% MeOH188.9% CH$_2$Cl$_2$/0.1% aq. NH$_3$ as eluent gave the sub-title compound (0.282 g).

Step c: N-{2-[4-(3,4-difluorophenoxy)-1-piperidinyl]propyl}-5-(2-pyridinyl)-2-thiophenesulfonamide.

Prepared by the method of Example 7, Step (d) using the product of Example 10, Step (b) to give the title compound as a solid (0.21 g).

$^1$H NMR: δ (DMSO) 0.91 (3H, d), 1.48–1.59 (2H, m), 1.84–1.89 (2H, m), 2.22–2.39 (2H, m), 2.56–2.61 (2H, m), 2.78–2.84 (1H, m), 2.91–2.98 (1H, m), 3.32 (1H, br s), 4.24–4.32 (1H, m), 6.71–8.59 (9H, m).

Melting point: 153–154° C.

EXAMPLE 11

This Example illustrates the preparation of N-{2-[4-(3,4-difluorophenoxy)-1-piperidinyl]ethyl}-N-methyl-5-(2-pyridinyl)-2-thiophenesulfonamide (Compound 8 of Table III).

Step a: N-{2-[4-(3,4-difluorophenoxy)-1-piperidinyl]ethyl}-2,2,2-trifluoroacetamide To the product of Example 4, Step (b) dissolved in CH$_2$Cl$_2$ (20 ml) with triethylamine (2.45 ml) at 0° C. was added trifluoroacetic anhydride (1.24 ml) in CH$_2$Cl$_2$ (5 ml). The reaction was allowed to warm to room temperature over 1 hr. The reaction mixture was diluted with CH$_2$Cl$_2$ and washed with H$_2$O. The combined organics were dried, filtered and solvents evaporated. Purification by flash silica column chromatography using 2% MeOH/97.6% CH$_2$Cl$_2$/0.4% aq. NH$_3$ as eluent gave the sub-title product (1.64 g).

MS: ESI(+ve): 353 (M+H)

Step b: N-{2-[-(3,4-difluorophenoxy)-1-piperidinyl]ethyl}-2,2,2-trifluoro-N-methylacetamide The product of Example 11, Step (a) (1.64 g) dissolved in THF (5 ml) was added dropwise to a suspension of NaH (60% dispersion in oil, 0.205 g) in THF (20 ml) at 0° C. The reaction mixture was allowed to warm to room temperature and stirred for 30 mins then cooled to 0° C. and methyl iodide (0.290 ml) dissolved in THF (5 ml) added dropwise. The reaction was then allowed to warm to room temperature and left for 12 hrs. Two further aliquots of methyl iodide (0.2 ml and 0.5 ml) were added over 12 hrs. The reaction was quenched with saturated NaHCO$_3$ and the product extracted with ethyl acetate, dried, and filtered. Evaporation of solvent and purification by flash silica column chromatography using 1% MeOH/98.5% CH$_2$Cl$_2$/0.5% aq. NH$_3$ as eluent gave the sub-title product (0.30 g).

MS: ESI(+ve): 367 (M+H)

Step c: N-{2-[4-(3,4-difluorophenoxy)-1-piperidinyl]ethyl}-N-methylamine

The product of Example 11, Step (b) (0.3 g) was dissolved in EtOH (15 ml) and NaOH (2M, 5 ml) added. The reaction was stirred for 48 hrs and H$_2$O and EtOAc added. The organic layer was washed with saturated aqueous NaCl solution, dried, filtered and evaporated to give an oil (0.221 g).

MS: ESI(+ve): 271 (M+H)

Step d: N-{2-[4-(3,4-difluorophenoxy)-1-piperidinyl]ethyl}-N-methyl-5-(2-pyridinyl)-2-thiophenesulfonamide hydrochloride.

Prepared by the method of Example 7, Step (d) using the product of Example 11, Step (c) with $Et_2O/HCl$ to give the title compound as a hydrochloride salt (0.073 g).

$^1$H NMR: δ ($D_2O$) 1.96–2.43 (2H, m), 2.92 (3H, s), 3.26–3.28 (1H, m), 3.41–3.63 (7H, m), 3.81–3.84 (1H, m), 6.82–6.87 (1H, m), 6.99–7.05 (1H, m), 7.23 (1H, m), 7.69 (1H, td), 7.83 (1H, d), 7.86 (1H, d), 8.08 (1H, d), 8.22 (1H, td), 8.60 (1H, ddd).

Melting point: 123° C.

EXAMPLE 12

This Example illustrates the preparation of 2-[4-(3,4-dichlorophenoxy)piperidin-1-yl]-N-[4-(methylsulfonyl)phenyl]ethanesulfonamide.

Step a: N-[4-(methylsulfonyl)phenyl]ethylenesulfonamide

To a suspension of 4-(methylsulfonyl)aniline (0.378 g) in diethyl ether (10 ml) and triethylamine (0.462 ml) at 0° C. was added 2-chloroethanesulfonyl chloride (0.346 ml). The reaction mixture was left to stir at 0° C. for 3 hrs and then at room temperature for 8 hrs. The solvent was evaporated to give the sub-title compound as a brown solid which was used without further purification in Example 12, step b.

MS: ES(–ve): 260 (M–H)

Step b: 2-[4-(3,4-dichlorophenoxy)piperidin-1-yl]-N-[4-(methylsulfonyl)phenyl]ethanesulfonamide The product from Example 12, step a was dissolved MeOH (10 ml) and the product of Example 1, step b) added, and the reaction stirred at room temperature for 2 hrs. The reaction mixture was then poured into water and the product extracted with dichloromethane. The combined organic extracts were washed with water and brine, then dried, filtered and concentrated. Purification by reverse phase HPLC {with a gradient eluent system [40% MeCN/$NH_4OAc_{aq}$ (0.1%) to 95% MeCN//$NH_4OAc_{aq}$ (0.1%)]}. Any excess $NH_4OAc$ in the product was removed by dissolving the compound in ethyl acetate and washing with aqueous saturated $NaHCO_3$ followed by drying of the organics, filtration and evaporation of solvent. This gave the title compound (0.052 g).

$^1$H NMR: δ(DMSO) 1.38–1.49 (2H, m), 1.72–1.82 (2H, m), 2.14–2.22 (2H, m), 2.52–2.62 (2H, m), 2.66–2.76 (2H, m), 3.20 (3H, s), 3.38–3.47 (2H, m), 4.30–4.42 (1H, m), 6.89–6.98 (1H, m), 7.22 (1H, d), 7.38 (2H, d), 7.48 (1H, d), 7.85 (2H, d).

MS: APCI(+ve): 507 (M+H)

EXAMPLE 13

Pharmacological Analysis: Calcium Flux $[Ca^{2+}]_i$ Assay

Human Eosinophils

Human eosinophils were isolated from EDTA anticoagulated peripheral blood as previously described (Hansel et al., J. Immunol. Methods, 1991, 145, 105–110). The cells were resuspended ($5\times10^6$ $ml^{-1}$) and loaded with 5 μM FLUO-3/AM+Pluronic F127 2.2 μl/ml (Molecular Probes) in low potassium solution (LKS; NaCl 118 mM, $MgSO_4$ 0.8 mM, glucose 5.5 mM, $Na_2CO_3$ 8.5 mM, KCl 5 mM, HEPES 20 mM, $CaCl_2$ 1.8 mM, BSA 0.1%, pH 7.4) for one hour at room temperature. After loading, cells were centrifuged at 200 g for 5 min and resuspended in LKS at $2.5\times10^6$ $ml^{-1}$. The cells were then transferred to 96 well FLIPR plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1% (v/v) DMSO. Assays were initiated by the addition of an $A_{50}$ concentration of eotaxin and the transient increase in fluo-3 fluorescence ($I_{Ex}$=490 nm and $I_{Em}$=520 nm) monitored using a FLIPR (Fluorometric Imaging Plate Reader, Molecular Devices, Sunnyvale, U.S.A.).

Human Eosinophil Chemotaxis

Human eosinophils were isolated from EDTA anticoagulated peripheral blood as previously described (Hansel et al., J. Immunol. Methods, 1991, 145, 105–110). The cells were resuspended at $10\times10^6$ $ml^{-1}$ in RPMI containing 200 IU/ml penicillin, 200 μg/ml streptomycin sulphate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton×100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Certain compounds of the Examples were found to be antagonists of the eotaxin mediated human eosinophil chemotaxis.

What is claimed is:

1. A compound of formula (I):

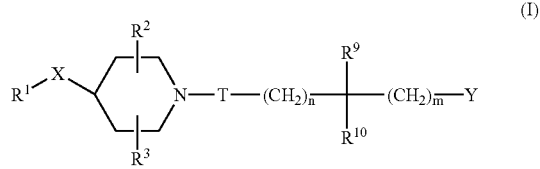

wherein: m and n are, independently, 0, 1, 2, 3 or 4; X is O; Y is $NR^4S(O)_2R^5$ or $S(O)_2NR^4R^5$; T is C=O or $CR^7R^8$; $R^1$ is hydrogen, $C_{1-6}$ alkyl, aryl or heterocyclyl; $R^2$ and $R^3$ are, independently, hydrogen or $C_{1-6}$ alkyl; $R^4$ and $R^6$ are, independently, hydrogen or $C_{1-6}$ alkyl (optionally substituted with aryl); $R^5$ is $C_{1-6}$ alkyl {optionally substituted by halogen, $CO_2R^{11}$, aryl or heterocyclyl}, $C_{3-10}$ cycloalkyl {optionally substituted by $C_{1-4}$ alkyl or oxo}, $C_{3-7}$ cycloalkenyl {optionally substituted by $C_{1-6}$ alkyl or aryl}, aryl or heterocyclyl; or, when Y is $S(O)_2NR^4R^5$, $R^5$ may also be hydrogen; $R^7$, $R^8$, $R^9$ and $R^{10}$ are, independently, hydrogen or $C_{1-6}$ alkyl (optionally substituted with aryl); wherein the foregoing aryl and heterocyclyl moieties are, independently, optionally substituted by one or more of halo, cyano, nitro, hydroxy, $S(O)_qR^{11}$, $OCONR^{12}R^{13}$, $NR^{14}R^{15}$, $NR^{16}COR^{17}$, $NR^{18}CONR^{19}R^{20}$, $SO_2NR^{21}R^{22}$, $NR^{23}SO_2R^{24}$, $CONR^{25}R^{26}$, $COR^{27}$, $CO_2R^{28}$, $OCOR^{29}$, $NR^{30}CO_2R^{31}$, $C_{1-6}$ alkyl (itself optionally substituted with halo, $C_{1-6}$ alkoxy, $C_{3-10}$ cycloalkyl, $CO_2(C_{1-6}$ alkyl), $OCO(C_{1-6}$ alkyl), $SO_2R^{32}$, $CONR^{33}R^{34}$, phenyl, phenoxy, heterocyclyl or heterocyclyloxy), $C_{3-10}$ cycloalkyl, $C_{1-6}$ alkoxy, $C_{1-6}$ haloalkoxy, $C_{2-6}$ alkenyl, $C_{2-6}$ alkynyl, methylenedioxy, phenyl, phenoxy, phenylthio, phenyl($C_{1-4}$)alkoxy, heterocyclyl, heterocyclyloxy or heterocyclyl($C_{1-4}$)alkoxy; wherein any of the immediately foregoing phenyl and heterocyclyl moieties are optionally substituted with halo, hydroxy, nitro, $S(O)_kC_{1-4}$ alkyl, $SO_2NH_2$, cyano, $C_{1-4}$ alkyl, $C_{1-4}$ alkoxy, $CONH_2$, $CONH(C_{1-4}$ alkyl), $CO_2H$, $CO_2(C_{1-4}$ alkyl), $NHCO(C_{1-4}$ alkyl), $NHSO_2(C_{1-4}$ alkyl), $CO(C_{1-4}$ alkyl), $CF_3$ or $OCF_3$; $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{26}$, $R^{27}$, $R^{28}$, $R^{29}$, $R^{30}$, $R^{31}$, $R^{33}$ and $R^{34}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); $R^{11}$, $R^{24}$ and $R^{32}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); k and q are, independently, 0, 1 or 2; or a pharmaceutically acceptable salt thereof.

2. A compound of formula (I) as claimed in claim 1 wherein aryl is phenyl.

3. A compound of formula (I) as claimed in claim 1 wherein heterocyclyl is furyl, thienyl, pyrrolyl, 2,5-dihydropyrrolyl, thiazolyl, pyrazolyl, oxazolyl, isoxazolyl, imidazolyl, piperidinyl, morpholinyl, pyridinyl, pyrimidinyl, indolyl, 2,3-dihydroindolyl, benzo[b]furyl, benz[b]thienyl, 2,3-dihydrobenz[b]thienyl, indazolyl, benzimidazolyl, benztriazolyl, benzoxazolyl, benzthiazolyl, 2,3-dihydrobenzthiazolyl, 1,2,3-benzothiadiazolyl, an imidazopyridinyl, thieno[3,2-b]pyridin-6-yl 1,2,3-benzoxadiazolyl, 2,1,3-benzothiadiazolyl, benzofurazan, quinoxalinyl, dihydro-1-benzopyryliumyl, 3,4-dihydro-1H-2,1-benzothiazinyl, a pyrazolopyridine, a purine, quinolinyl, isoquinolinyl, a naphthyridinyl, a benzothiazinyl, benzo[d]imidazo[2,1-b]thiazol-2-yl or dibenzothiophenyl; or such a group, where appropriate, in the form of an N-oxide, an S-oxide or an S-dioxide.

4. A compound of formula (I) as claimed in claim 1, wherein T is C=O or $CR^7R^8$, wherein $R^7$ and $R^8$ are, independently, hydrogen or $C_{1-4}$ alkyl.

5. A compound of formula (I) as claimed in claim 1 wherein n is 0 or 1.

6. A compound of formula (I) as claimed in claim 1 wherein m is 0.

7. A compound of formula (I) as claimed in claim 1, wherein R1 is phenyl substituted with one or more of fluorine, chlorine, $C_{1-4}$ alkyl or $C_{1-4}$ alkoxy.

8. A compound of formula (I) as claimed in claim 1 wherein $R^2$ and $R^3$ are both hydrogen.

9. A compound of formula (I) as claimed in claim 1 wherein $R^4$ is hydrogen or $C_{1-4}$ alkyl.

10. A compound of formula (I) as claimed in claim 1 wherein $R^9$ is hydrogen, $C_{1-4}$ alkyl or phenyl($C_{1-4}$ alkyl).

11. A compound of formula (I) as claimed in claim 1 wherein $R^{10}$ is hydrogen.

12. A compound of formula (I) as claimed in claim 1 wherein $R^5$ is $C_{1-6}$ alkyl {optionally substituted by phenyl (itself optionally substituted by halogen or nitro), $CO_2(C_{1-4}$ alkyl), $C_{3-10}$ cycloalkyl (itself optionally substituted by oxo or $C_{1-4}$ alkyl) or heterocyclyl}, aryl {optionally substituted by halogen, $C_{1-6}$ alky, $C_{1-4}$ alkoxy, OH, nitro, cyano, $CF_3$, $OCF_3$, $N(C_{1-4}$ alkyl)$_2$, $NHCO(C_{1-4}$ alkyl), $CO_2H$ or $CO_2(C_{1-4}$ alkyl)} or hererocyclyl {optionally substituted by halogen, oxo, $C_{1-4}$ alkyl, $NHCO(C_{1-4}$ alkyl), $CO(C_{1-4}$ alkyl), $CO_2H$, $CO_2(C_{1-4}$ alkyl), pyridyl or isoxazolyl}.

13. A compound of formula (I) as claimed in claim 1 wherein Y is $NR^4S(O)_2R^5$.

14. A pharmaceutical composition which comprises a therapeutically effective amount of a compound of the formula (I), or a pharmaceutically acceptable salt thereof, as claimed in claim 1, and a pharmaceutically acceptable adjuvant, diluent or carrier.

15. A method of treating asthma or rhinitis in a patient suffering from, said disease, which comprises administering to the patient a therapeutically effective amount of a compound of formula (I), or a pharmaceutically acceptable salt thereof, as claimed in claim 1.

16. A process for preparing a compound of formula (I) as claimed in claim 1, the process comprising:

a) coupling a compound of formula (II):

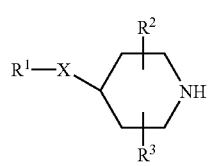

(II)

with a compound of formula (III):

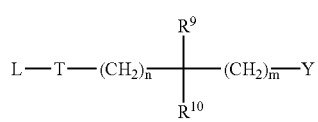

(III)

wherein L is a suitable leaving group, when Y is $NR^4S(O)_2R^5$ then $R^4$ is not hydrogen, when Y is $S(O)_2NR^4R^5$ then neither $R^4$ nor $R^5$ is hydrogen and T is optionally protected during the course of the reaction by a standard protecting group;

b) for preparing a compound of formula (I) wherein Y is NR⁴S(O)₂R⁵, reacting a compound of formula (V):
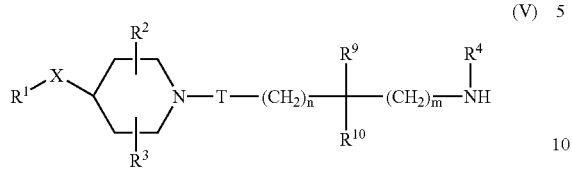
with a suitable sulphonyl chloride of formula ClSO₂R⁵; or,
c) for preparing a compound of formula (I) wherein m and n are both 0, T is CH₂, R⁹ and R¹⁰ are both hydrogen and Y is S(O)₂NR⁴R⁵, reacting a compound of formula (II) with a compound of formula (IX):
in a suitable solvent.
* * * * *

UNITED STATES PATENT AND TRADEMARK OFFICE
CERTIFICATE OF CORRECTION

PATENT NO. : 7,348,341 B2 Page 1 of 1
APPLICATION NO. : 10/296034
DATED : March 25, 2008
INVENTOR(S) : Hitesh Sanganee and Brian Springthorpe It is certified that error appears in the above-identified patent and that said Letters Patent is hereby corrected as shown below:

Title Page, Column 2
FOREIGN PATENT DOCUMENTS
Line 5, after "03264579", change "11/1999" to --11/1991--.

Title Page, Column 2
FOREIGN PATENT DOCUMENTS
Line 22, delete "WO WO 03/018556* 3/2003".

Title Page, Column 2
FOREIGN PATENT DOCUMENTS
Line 23, delete "WO WO 03/018566* 3/2003".

Title Page, Column 2
OTHER PUBLICATIONS
Line 18, delete "treatmant" insert --treatment--.

Column 26,
Line 2, delete "R1" and insert --$R^1$--.
Line 22, delete "hererocyclyl" and insert --heterocyclyl--.
Lines 64-65, delete "$S(O)^2$" insert --$S(O)_2$--.

Signed and Sealed this

Twenty-fourth Day of June, 2008

JON W. DUDAS
*Director of the United States Patent and Trademark Office*